(12) United States Patent
Habif et al.

(10) Patent No.: US 6,428,775 B1
(45) Date of Patent: Aug. 6, 2002

(54) NON-GREASY MAKE-UP REMOVER

(75) Inventors: Stephan Samuel Habif, Demarest, NJ (US); Jose Antonio Revilla-Lara, Temixco (MX); Humberto Garcia Ruiz, Cuernavaca (MX); Luisa Argelia Carrera Chavez, Cuernavaca (MX); Jose Manuel Lopez-Gallo Gomez, Cuernavaca (MX)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/696,422

(22) Filed: Oct. 25, 2000

Related U.S. Application Data

(60) Provisional application No. 60/161,439, filed on Oct. 16, 1999.

(51) Int. Cl.[7] .......................... A61K 7/025; A61K 6/00; A61K 7/00
(52) U.S. Cl. ...................... 424/64; 424/70.1; 424/401
(58) Field of Search ............................... 424/401, 70.7, 424/64; 514/844, 845

(56) References Cited

U.S. PATENT DOCUMENTS 5,888,951 A * 3/1999 Gagnebien et al. ......... 510/130

FOREIGN PATENT DOCUMENTS

| EP | 422 862 | 4/1991 |
|----|---------|--------|
| EP | 1 034 774 | 9/2000 |

OTHER PUBLICATIONS

PCT International Search Report in a PCT application PCT/EP 00/09646.

* cited by examiner

Primary Examiner—Thurman K. Page
Assistant Examiner—S. Howard
(74) Attorney, Agent, or Firm—Ellen Plotkin

(57) ABSTRACT

A make-up remover which has high efficacy yet low greasiness, contains a combination of two make-up removal ingredients: (i) mineral oil and/or wax and (ii) isoparaffin, wherein the second ingredient (ii) boosts the make-up removal capacity of the first ingredient, thus allowing to decrease the level of mineral oil and/or wax in the composition, which in turn results in decreased greasiness of the composition.

5 Claims, No Drawings

NON-GREASY MAKE-UP REMOVER

This application claims the benefit of U.S. provisional application No. 60/161,439 filed Oct. 26, 1999.

FIELD OF THE INVENTION

Non-greasy cosmetic composition with effective make-up removal properties.

BACKGROUND OF THE INVENTION

Removing mascara, lipstick, and other make-up from the face is a daily task for many women. The modern trend is to make mascara and lipstick that is resistant to rub-off or moisture, hence increasing the challenge of make-up removal. An oil-based mascara is one of the most difficult types of make-up to remove.

Currently, one of the most popular cosmetic products to remove make-up is the so-called "cold cream." Cold cream is applied to the skin like a regular cream; the slight massaging during application results in the solubilization of make-up and other impurities from the skin into the cream which is subsequently wiped-off using a cotton ball or a tissue. Cold creams contain a high level of oil (i.e., as much as 50% mineral oil). Oil is very effective for make-up removal, because most make-up products are oil-based and thus dissolve or bind to oil. Unfortunately, high levels of oil also result in a poor acceptability from consumers due to the high level of greasiness/oiliness imparted by the product. It is highly desirable to obtain a make-up remover which has high efficacy yet low greasiness.

SUMMARY OF THE INVENTION

The present invention includes a cosmetic make-up removal composition comprising:
 (i) less than about 50% of a first make-up removing ingredient selected from the group consisting of waxes, mineral oil and mixtures thereof,
 (ii) an isoparaffin as a second make-up removing ingredient; and
 (iii) a cosmetically acceptable vehicle.

The inventive compositions contain a combination of two make-up removal ingredients, wherein the second ingredient (ii) boosts the make-up removal capacity of the first ingredient, thus allowing to decrease the content of mineral oil and/or wax in the composition, which in turn result in decreased greasiness of the composition.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the oil-in-water emulsion, unless otherwise specified.

The term "skin" as used herein includes the skin on the face, neck, chest, back, arms, hands, legs and scalp.

For the avoidance of doubt the word "comprising" is intended to mean including but not necessarily consisting of or composed of. In other words the listed steps or options need not be exhaustive.

The inventive compositions contain a first make-up removal ingredient, which is mineral oil, alone or in combination with waxes, such as ceresine wax and paraffin wax. Mineral oil and/or wax is a greasy material. In the present invention, by virtue of the inclusion of an isopaffin, the content mineral oil and/or wax is minimized to below 50%. Preferably, in order to minimize greasiness, yet to maintain efficacy, mineral oil and/or wax is employed in an amount ranging from 10 to 49%, more preferably the amount is in the range of from 10 to 40%, most preferably 10 to 30%, and optimally from 15 to 25%.

The second make-up removal ingredient included in the present invention is an isoparaffin. According to the present invention, isoparaffins enhance make-up removing capacity of mineral oil and/or wax, without contributing to the greasiness of the final product. Isopaffins are branched aliphatic saturated hydrocarbon molecules. Isoparaffins within the scope of this invention preferably contain from 7 and to 20 carbon atoms, more preferably from 10 to 20 carbons, most preferably from 11 to 16 carbons. Isoparaffin is generally included in the inventive compositions in an amount of at least 5%, preferably present in an amount of from 5% to 40%, more preferably from 5% to 20%, most preferably from 7% to 15%.

The compositions according to the invention also comprise a cosmetically acceptable vehicle to act as a dilutant, dispersant or carrier for the make-up removing ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes. Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
 (1) Alkenyl or alkyl esters of fatty acids having 10 to 20 carbon atoms. Examples thereof include isoarachidyl neopentanoate, isononyl isononanoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monoesters, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

These emollients may have a MUR ability and therefor may be included as part of the MUR combination of ingredients.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

Optional Skin Benefit Materials and Cosmetic Adjuncts

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di- $C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Various types of additional active ingredients may be present in cosmetic compositions of the present invention. Actives are defined as skin benefit agents other than emollients and other than ingredients that merely improve the physical characteristics of the composition. Although not limited to this category, general examples include additional anti-oxidants, anti-aging ingredients and sunscreens.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Many cosmetic compositions, especially those containing water, must be protected against the growth of potentially harmful microorganisms. Preservatives are, therefore, necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the composition.

Powders may be incorporated into the cosmetic composition of the invention. These powders include chalk, talc, Fullers earth, kaolin, starch, smectites clays, chemically modified magnesium aluminum silicate, organically modified montmorillonite clay, hydrated aluminum silicate, fumed silica, aluminum starch octenyl succinate and mixtures thereof.

The composition according to the invention is intended primarily as a product for topical application to human skin, especially as an agent for removing make-up.

In use, a quantity of the composition, for example from 1 to 100 ml, is applied to exposed areas of the skin, from a suitable container or applicator and, if necessary, it is then spread over and/or rubbed into the skin using the hand or fingers or a suitable device.

The inventive compositions are particularly useful for removing all type of make up, such as lipstick, foundation, eyeliner, mascara, etc.

Product Form and Packaging

The cosmetic skin composition of the invention can be in any form, e.g. formulated as a gel, lotion, a fluid cream, or a cream. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The following specific examples further illustrate the invention, but the invention is not limited thereto.

EXAMPLES

The following methods to evaluate make-up removal capacity and greasiness were employed in the examples below.

Make-up Removal Efficacy Test ("MUR")

Subjects: 10 subjects, male and female

Test material: Revlon Colorstay Mascara (01 Blackest Black)

Measurements: Minolta CR-10 Chromameter set to the $L^*$, $a^*$, $b^*$ color system. Chromameter measures the skin color in three axes $L^*$ $a^*$ $b^*$. Visual grading of the amount of color cosmetic in the skin using the following scale:

0=None
½=Questionable; trace with spotty coverage
1=Trace with uniform coverage
2=Slight with uniform coverage
3=Moderate with uniform coverage
4=Heavy with uniform coverage Products: Up to six different products can be tested.

Six 3.5×2.5 cm sites are selected in the inner forearm. The first readings are taken (CLEAN).

Mascara is applied to the forearm.

The application is visually, graded as 4 (heavy with uniform coverage). Mascara was spread uniformly using spatula for even coverage.

Mascara is spread on the forearm using the spatula or brush and allowed to dry for 12 minutes. The test product is applied with a precision pipette (aprox. 0.5 g).

Twelve minutes after application, the second readings are taken (MAKE- UP).

Mascara is removed from each site with a different test product. The test product is applied with a precision pipette to ensure the same quantity of product is applied on each site to remove the mascara.

The make up is removed by the same person using circular motion during 20 seconds, and removed with a tissue.

The final readings are taken (REMOVED).

Calculation of Product Efficacy $$\text{Percent Removed (Chromameter)} = \frac{\sqrt{[(L_{Makeup} - L_{Removed})^2 + (a_{Makeup} - a_{Removed})^2 + (b_{Makeup} - b_{Removed})^2]}}{\sqrt{[(L_{Makeup} - L_{Clean})^2 + (a_{Makeup} - a_{Clean})^2 + (b_{Makeup} - b_{Clean})^2]}} \times 100$$

Percent Removed (Visual)=$(\overline{X}_{Makeup} - \overline{X}_{Removed})/(\overline{X}_{Makeup} - \overline{X}_{Clean}) \times 100$ In the examples, chromameter values were used to calculate product efficacy. Although chromameter values were used, visual grades correlate very well with chromameter.

Greasiness Evaluation

Significance level: Alfa 0.05=95% Confidence Level.

Subjects: 30 subjects, female, Expert Panel.

All subjects evaluated the products. Order of presentation was rotated among panelists. The subjects evaluated "final greasiness"

Final greasiness is evaluated considering the shining of the skin due to the product and the greasy sensation on the hands after two minutes of application.

Final greasiness was scored from 0 to 10, whereas 0 meant "not greasy" and 10 meant "very greasy."

MUR Criteria: A formulation was considered as a good Make-up Remover at MUR of at least 70% for mascara, with MUR above 85% considered outstanding. Greasiness Criteria: The criteria for low greasiness was at most 6.5 preferably 6 or below.

In the Examples below, isoparaffins and mineral oil and waxes were obtained from the following suppliers:

| CHEMICAL NAME | COMMERCIAL NAME | SUPPLIER |
|---|---|---|
| Ceresin Wax | Ceresina | Multiceras |
| Mineral Oil | Aceite mineral 70 | Quimicos y Derivados/ Comisionistas Quimicos |
| Isoparaffin C11–C13 | Isopar L | Exxon |
| Isoparaffin C7–C8 | Isopar C | Exxon |
| Isoparaffin C13–C14 | Isopar M | Exxon |
| Isoparaffin C12–C20 | Isopar V | Exxon |
| Isoparaffin C16 | Arlamol HD | Uniquema |

Example 1

This example evaluated make-up removal capacity ("MUR") and greasiness of make-up removal compositions containing various amounts of mineral oil. None of the compositions contained an isoparaffin, so none were within the scope of the present invention.

Compositions A–E were prepared in Table 1 B were prepared, each containing ingredients in Table 1 A in addition to those listed in Table 1 B.

TABLE 1A

| Ingredient | % |
| --- | --- |
| Beeswax | 2.315 |
| Sodium Borate | 1.895 |
| Montan Acid Wax | 0.780 |
| Behenic Acid | 0.780 |
| Cetyl Alcohol | 0.465 |
| Fragrance | 0.350 |
| Ceteth-20 | 0.307 |
| Carbomer | 0.248 |
| Methylparaben | 0.200 |
| Propylparaben | 0.100 |

TABLE 1B

| | A | B | C | D | E |
| --- | --- | --- | --- | --- | --- |
| Water | 72.560 | 62.560 | 52.560 | 42.560 | 36.403 |
| Mineral Oil | 20.000 | 30.000 | 40.000 | 50.000 | 50.000 |
| Ceresin wax | — | — | — | — | 6.157 |
| MUR % | 47.2 | 46.4 | 71.4 | 79.1 | 86 |
| Greasiness | 5.0 | 5.9 | 5.9 | 6.8 | 7.5 |

It can be seen from the results in Table 1B that compositions with less than 50% of mineral oil (compositions A–C) had unacceptably low MUR, while compositions with 50% or more mineral oil (D and E) were too greasy.

Example 2

This example investigated the effect of various ingredients on MUR and greasiness.

Compositions containing ingredients in Table 2B in addition to ingredients of Table 2A were prepared.

TABLE 2A

| Ingredient | % |
| --- | --- |
| Water | 62.560 |
| Mineral Oil | 20.000 |
| Beeswax | 2.315 |
| Sodium Borate | 1.895 |
| Montan Acid Wax | 0.780 |
| Behenic Acid | 0.780 |
| Cetyl Alcohol | 0.465 |
| Fragrance | 0.350 |
| Ceteth-20 | 0.307 |
| Carbomer | 0.248 |
| Methylparaben | 0.200 |
| Propylparaben | 0.100 |

TABLE 2B

| | F | G | H | I | J | K |
| --- | --- | --- | --- | --- | --- | --- |
| Ingredient | Isoparaffin C11–C13 | Cyclotetra-Siloxane | Cyclopenta-siloxane | Polyethylene glycol (600) | Myristyl Myristate | 2 Methyl-1, 3-Propanediol |
| % | 10.000 | 10.000 | 10.000 | 10.000 | 10.000 | 10.000 |
| MUR % | 89.3 | 68.5 | 57.7 | 55.8 | 57.2 | 33.2 |
| Greasiness | 5.0 | — | — | — | — | — |

It can be seen from the results in Table 2B that only composition within the scope of the invention containing an isoparaffin (F) achieved acceptable MUR and greasiness. Compositions G–K, not within the scope of the invention, which employed ingredients other than isoparaffin, had unacceptably low MUR. Composition F had substantially improved MUR compared to composition A in Example 1-both contained mineral oil at 20%, but composition F additionally included an isoparaffin.

Example 3

This example investigated the effect of various chain lengths isoparaffins on MUR and greasiness.

Compositions were prepared (all within the scope of the invention) which contained ingredients as listed in Table 2A and in Table 3.

TABLE 3

| Ingredient | Isoparaffin C7–C8 | Isoparaffin C11–C13 | Isoparaffin C16 | Isoparaffin C12–C20 |
| --- | --- | --- | --- | --- |
| % | 10.000 | 10.000 | 10.000 | 10.000 |
| MUR % | 83.1 | 89.3 | 85.5 | 71.6 |
| Greasiness | — | 5.0 | 6.1 | — |

It can be seen from the results in Table 3 that isoparaffins of various chain legths were effective, with C11–C16 isoparaffins achieving the best MUR while maintaining low greasiness.

Example 4

This example investigated the effect of various weight amounts of isoparaffins on MUR and greasiness.

Compositions were prepared containing ingredients indicated in Table 4B and ingredients listed in Table 4A.

TABLE 4A

| Ingredient | % |
| --- | --- |
| Water | Up to 100 |
| Mineral Oil | 20.000 |
| Beeswax | 2.315 |
| Sodium Borate | 1.895 |
| Montan Acid Wax | 0.780 |
| Behenic Acid | 0.780 |
| Cetyl Alcohol | 0.465 |
| Fragrance | 0.350 |
| Ceteth-20 | 0.307 |
| Carbomer | 0.248 |
| Methylparaben | 0.200 |
| Propylparaben | 0.100 |

TABLE 4B

| Ingredient | Isoparaffin C11–C13 | Isoparaffin C11–C13 | Isoparaffin C11–C13 | Isoparaffin C16 | Isoparaffin C16 | Isoparaffin C16 |
|---|---|---|---|---|---|---|
| % | 7.000 | 10.000 | 15.000 | 3.000 | 7.500 | 10.000 |
| MUR % | 88.6 | 89.3 | 93.3 | 69.3 | 85.6 | 85.5 |
| Greasiness | — | 5.0 | — | — | — | 6.1 |

It can be seen from the results in Table 4B that all the amounts tested were effective and that the efficacy increased at levels above 3%.

Example 5

This example investigated the efficacy and greasiness of different compositions containing the same isoparaffins.

Compositions were prepared (all within the scope of the invention) containing ingredients as indicated in Table 5C. Compositions in Table 5C contained ingredients of either Table 5A or 5B.

TABLE 5A

| Ingredient | % |
|---|---|
| Water | 62.560 |
| Mineral Oil | 20.000 |
| Beeswax | 2.315 |
| Sodium Borate | 1.895 |
| Montan Acid Wax | 0.780 |
| Behenic Acid | 0.780 |
| Cetyl Alcohol | 0.465 |
| Fragrance | 0.350 |
| Ceteth-20 | 0.307 |
| Carbomer | 0.248 |
| Methylparaben | 0.200 |
| Propylparaben | 0.100 |

TABLE 5B

| Ingredient | % |
|---|---|
| Water | 65.231 |
| Mineral Oil | 20.000 |
| Cetyl Alcohol | 1.000 |
| Ceteth-20 | 1.000 |
| Cetearyl Alcohol | 1.000 |
| Glyceryl Stearate | 0.500 |
| Triethanolamine | 0.371 |
| Fragrance | 0.350 |
| Carbomer | 0.248 |
| Methylparaben | 0.200 |
| Propylparaben | 0.100 |

TABLE 5C

| | TABLE 5A Ingredients | TABLE 5B Ingredients | TABLE 5B Ingredients | TABLE 5A Ingredients | TABLE 5B Ingredients |
|---|---|---|---|---|---|
| Ingredient | Isoparaffin C11–C13 | Isoparaffin C11–C13 | Isoparaffin C13–C14 | Isoparaffin C16 | Isoparaffin C16 |
| % | 10.000 | 10.000 | 10.000 | 10.000 | 10.000 |
| MUR % | 87.7 | 89.3 | 87.3 | 84.0 | 85.5 |
| Greasiness | — | — | 5.0 | — | 6.1 |

It can be seen from the results in Table 5C that same isoparaffins were effective in either composition 5A or 5B.

Example 6

The following additional composition within the scope of the invention was prepared.

| Ingredient | % |
|---|---|
| Water | 55.531 |
| Minerol Oil | 30.000 |
| Isoparaffin C16 | 7.000 |
| Glycerin | 3 |
| Cetyl Alcohol | 1.100 |
| Ceteth-20 | 1.000 |
| Cetearyl Alcohol | 0.600 |
| Glyceryl Stearate | 0.500 |
| Phenoxyethanol; | 0.400 |
| Methylparaben; | |
| Isopropylparaben; | |
| Isobutylparaben: | |
| Butylparaben | |
| Triethanolamine | 0.371 |
| Carbomer | 0.248 |
| Fragrance | 0.240 |
| Cucumber extract | 0.010 |
| MUR | 88.2% |
| Greasiness | 6.5 |

It should be understood that the specific forms of the invention herein illustrated and described are intended to be representative only. Changes, including but not limited to those suggested in this specification, may be in the illustrated embodiments without departing from the clear teachings of the disclosure. Accordingly, reference should be made to the following appended claims in determining the full scope of the invention.

What is claimed is:

1. A cosmetic make-up removal composition consisting essentially of:

(i) about 15 to about 25% of a first make-up removing ingredient selected from the group consisting of waxes, mineral oil and mixtures thereof, (ii) at least about 5% of an isoparaffin as a second make-up removing ingredient; and (iii) a cosmetically acceptable vehicle.

2. The composition of claim 1 wherein the first make-up removing ingredient is mineral oil.

3. The composition of claim 1 wherein the isoparaffin is selected from C7 to C20 isoparaffins.

4. The composition of claim 1 wherein the isoparaffin is present in an amount of from 5 to 40%.

5. A method of removing make-up, the method comprising applying to the skin the composition of claim 1.

* * * * *